(12) United States Patent
Jensen

(10) Patent No.: US 9,376,358 B2
(45) Date of Patent: Jun. 28, 2016

(54) SYSTEM AND METHOD FOR REMOVAL OF HEAVY METAL IONS FROM A RICH HYDRATE INHIBITOR STREAM

(71) Applicant: Fjords Processing AS, Lysaker (NO)

(72) Inventor: Kristian Jensen, Asker (NO)

(73) Assignee: FJORDS PROCESSING AS, Lysaker (NO)

( * ) Notice: Subject to any disclaimer, the term of this patent is extended or adjusted under 35 U.S.C. 154(b) by 0 days.

(21) Appl. No.: 14/404,519

(22) PCT Filed: May 29, 2013

(86) PCT No.: PCT/IB2013/054428
§ 371 (c)(1),
(2) Date: Nov. 28, 2014

(87) PCT Pub. No.: WO2013/179236
PCT Pub. Date: Dec. 5, 2013

(65) Prior Publication Data
US 2015/0112102 A1   Apr. 23, 2015

(30) Foreign Application Priority Data
May 30, 2012  (NO) .................................. 20120634

(51) Int. Cl.
| | | |
|---|---|---|
| *C07C 29/88* | (2006.01) | |
| *B01J 14/00* | (2006.01) | |
| *E21B 21/06* | (2006.01) | |
| *C09K 8/52* | (2006.01) | |
| *B04B 7/12* | (2006.01) | |
| *B01J 4/00* | (2006.01) | |
| *B04B 1/04* | (2006.01) | |
| *B01D 21/26* | (2006.01) | |

(52) U.S. Cl.
CPC .................. *C07C 29/88* (2013.01); *B01J 4/001* (2013.01); *B01J 14/00* (2013.01); *B04B 1/04* (2013.01); *B04B 7/12* (2013.01); *C09K 8/52* (2013.01); *E21B 21/068* (2013.01); *B01D 21/262* (2013.01); *C09K 2208/22* (2013.01)

(58) Field of Classification Search
CPC ....................................................... C07C 29/88
See application file for complete search history.

(56) References Cited

U.S. PATENT DOCUMENTS

| | | | |
|---|---|---|---|
| 3,529,767 A | 9/1970 | Keith, Jr. et al. | |
| 4,013,519 A | 3/1977 | Hoppert et al. | |
| 4,915,818 A | 4/1990 | Yan | |
| 5,049,285 A * | 9/1991 | Somerville et al. | ........... 210/710 |
| 5,158,651 A | 10/1992 | Doerr | |
| 5,422,008 A | 6/1995 | Woyciesjes et al. | |
| 6,340,373 B1 | 1/2002 | Billington | |
| 7,435,338 B2 * | 10/2008 | Carnell | ........................ 208/253 |
| 2005/0072663 A1 | 4/2005 | Laborie et al. | |
| 2008/0283470 A1 | 11/2008 | Gustafsson et al. | |
| 2010/0019023 A1 | 1/2010 | Silverstein et al. | |
| 2012/0018293 A1 | 1/2012 | Kaasa et al. | |

FOREIGN PATENT DOCUMENTS

| | | |
|---|---|---|
| DE | 36 19 926 | 1/1987 |
| EP | 0 546 740 | 6/1993 |
| GB | 2473213 | 3/2011 |
| WO | 2005/092470 | 10/2005 |

OTHER PUBLICATIONS

International Search Report issued Oct. 17, 2013 in International Application No. PCT/IB2013/054428.
Norwegian Search Report issued Dec. 19, 2012 in corresponding Norwegian patent application No. 20120634.

* cited by examiner

*Primary Examiner* — Brian J Davis
(74) *Attorney, Agent, or Firm* — Wenderoth, Lind & Ponack, L.L.P.

(57) ABSTRACT

Method and system for removal of heavy metal ions from a rich hydrate inhibitor stream, wherein the method comprises a) adding a selective heavy metal reactant to the rich hydrate inhibitor stream, forming a fluid stream comprising heavy metal salt particles, b) separating the obtained fluid stream in three streams a hydrocarbon stream, a recovered rich hydrate inhibitor stream, and a slurry comprising the heavy metal salt particles, c) separating remaining hydrate inhibitor from the slurry thereby obtaining a concentrated rest comprising the heavy metal salt particles.

10 Claims, 4 Drawing Sheets

SYSTEM AND METHOD FOR REMOVAL OF HEAVY METAL IONS FROM A RICH HYDRATE INHIBITOR STREAM

The present invention relates to a method for removal of heavy metal ions from a rich hydrate inhibitor stream and a heavy metal ions removal system. Especially the present invention relates to a method for controlled precipitation of heavy metal ion salts so that they are obtained as a separate fraction.

BACKGROUND

It is well known that well streams containing a mixture of fluids such as crude oil, condensate, formation water and gas during transportation may react and form solid hydrates resulting in i.e. blocked pipelines. To avoid and or limit the formation of these, hydrate inhibitors are added to the well stream prior to transportation. One often applied hydrate inhibitor is mono-ethylene glycol (MEG); other applicable hydrate inhibitors include glycol compounds with other substituents, as well as kinetic hydrate inhibitors or a combination thereof. The term kinetic refers to the effect of the inhibitor lowering the reaction rate of the hydrate forming reactions.

Hydrate inhibitors such as MEG are valuable chemicals and the recycling thereof provides reduced costs. A number of different steps and methods for separating MEG for reuse are known in the art. An obstacle for the regeneration process is degradation of the inhibitor at high temperatures which limits the possibility to use heating to obtain separation.

The recovered well stream will comprise not only the desired hydrocarbons, hydrate inhibitor, employed chemicals such as pH stabilizer and formation water, but also different ions dissolved from the formation. Traditional hydrate inhibitor recovery and reclamation systems have been developed to remove ions in the form of precipitated salts from the recovered hydrate inhibitor to control the salt concentration and allow for continued reuse of the hydrate inhibitor. The most common precipitated salts are chlorides, carbonates or hydroxides of Na, K, Ca, Mg, Fe or Ba. These precipitated salts are not considered especially harmful and the safe handling thereof can be relatively easily secured. Recently, however there has been discovered a number of formations which comprise heavy metals including mercury in such a form that the mercury ions are included in the well stream. In a traditional system the mercury ions will follow the hydrate inhibitor into the reclamation system and be precipitated in the form of mercury salts together with the other salts present in the rich hydrate inhibitor stream. However the separated salts will be a mixture comprising mercury salts and the total salt mixture must be treated as hazardous waste. In a standard traditional MEG reclamation system the amounts of salts removed per day is in the range 1 to 20 tonnes/day. The main part of the salts is NaCl. If heavy metal salts are introduced in this mixture then the total salts produced become hazardous waste that requires special treatment. This is very demanding especially on offshore installations.

PRIOR ART

Different technical solutions have been developed to extract inhibitor and handle the inorganic salt problem. Examples of these techniques are disclosed in U.S. Pat. No. 6,340,373 and US2005/0072663 and US2010/019023.

OBJECTIVES OF THE INVENTION

The objective of the present invention is to provide a method and a system applicable to reduce the amount of hazardous waste produced from regeneration of hydrate inhibitor streams comprising heavy metals.

A further goal is to minimize the process part and the process equipment that is handling process streams comprising hazardous heavy metals or metal ions.

It is also a goal to provide a process with limited negative or even positive influence on the efficiency of the downstream processes.

Another intension is to provide a method and system which can be retrofitted on existing systems or included in the new process.

The present invention provides a method for removal of heavy metal ions from a rich hydrate inhibitor stream, wherein the method comprises a) adding a selective heavy metal reactant to the rich hydrate inhibitor stream, forming a fluid stream comprising heavy metal salt particles, b) separating the obtained fluid stream in three streams a hydrocarbon stream, a recovered rich hydrate inhibitor stream, and a slurry comprising the heavy metal salt particles, c) separating remaining hydrate inhibitor from the slurry thereby obtaining a concentrated rest comprising the heavy metal salt particles.

The recovered rich hydrate inhibitor stream is substantially heavy metal free. The recovered rich hydrate inhibitor stream can be further processed according to well known processes for regeneration of rich hydrate inhibitor to obtain lean hydrate inhibitor applicable for reuse. The recovered rich hydrate inhibitor stream comprises in addition to the hydrate inhibitor water and non-heavy metal salts, and depending on the separation efficiency of step b) the recovered rich inhibitor may or may not contain a hydrocarbon rest.

In one aspect of the method according to the present invention the separation in step b) is performed in a disc stack centrifuge.

In another aspect of the present invention the method comprises regulating the pH of the rich hydrate inhibitor stream to between 6 and 8.

In yet another aspect the method comprises regulating the temperature of the rich hydrate inhibitor stream to below 30° C.

The regulation of the pH close to neutral and having low temperature provides favourable condition for heavy metal precipitation at the same time limiting possibly avoiding precipitation of other divalent cations such as Fe, Ca, Ba, Sr, Mg.

In a further aspect of the method according to the present invention the heavy metal is selected from the group mercury, cadmium, lead, chromium, cobalt, arsenic, nickel, manganese and copper, preferably mercury.

In yet another aspect the method comprises combining the remaining hydrate inhibitor with the recovered rich hydrate inhibitor stream.

In a further aspect of the method the selectivity of the reactant and the control of pH and temperature other divalent cations such as Fe, Ca, Ba, Sr, Mg are dissolved in the hydrate inhibitor through out the heavy metal removal. The method may accordingly further comprise downstream precipitation and removal of divalent cation salts from the recovered rich hydrate inhibitor stream.

In a specific aspect of the present invention the selective heavy metal reactant is a sulphide, preferably $Na_2S$.

In another aspect of the invention the method further comprises adding a flocculent to the rich hydrate inhibitor stream.

Further in one aspect of the invention the hydrate inhibitor is a glycol based inhibitor, especially the hydrate inhibitor is mono-ethylene-glycol (MEG).

The present invention further provides a rich hydrate inhibitor heavy metal ions removal system comprising a reaction tank with a rich hydrate inhibitor inlet, at least one heavy metal ions reactant inlet, and a reacted rich hydrate inhibitor outlet in fluid communication with a three phase disc stack centrifuge comprising a hydrocarbon outlet, a recovered hydrate inhibitor outlet and a slurry outlet.

In one aspect of the removal system according to the invention the system further comprises a separation unit with an inlet in fluid communication with the slurry outlet, a heavy metal salt outlet and a remaining hydrate inhibitor outlet.

In another aspect the system comprises a fluid line with an inlet in fluid communication with the remaining hydrate inhibitor outlet and an outlet in fluid communication with the recovered hydrate inhibitor outlet and a pretreatment system.

In yet another embodiment the removal system comprises a return loop for regulated returning of the remaining hydrate inhibitor upstream the separation unit. The return loop allows for returning of remaining hydrate inhibitor from the remaining inhibitor outlet to the separation unit if the separation achieved was not effective enough.

Further the removal system may comprise a return line with an inlet in fluid communication with the remaining hydrate inhibitor outlet and an outlet in fluid communication with the reacted hydrate inhibitor outlet and the three phase disc stack centrifuge.

The term "heavy metals" as used here refers to environmental toxic heavy metals. The term covers for instance the elements mercury, cadmium, lead, chromium, cobalt, arsenic, nickel, manganese and copper.

The term "heavy metal ions" refer to ions of the above defined heavy metals.

The term "hydrate inhibitor" as employed here refers to hydrate inhibitors such as glycol based inhibitors like mono-ethylene-glycol (MEG), di-ethylene-glycol (DEG) and tri-ethylene-glycol (TEG), tetra-ethylene-glycol (TREG) or combinations thereof. The term also refers to kinetic hydrate inhibitors, named so after by their ability to slow down the hydrate forming reactions and well known in the art or any combination of glycol based inhibitor(s) and kinetic inhibitors.

The term "rich hydrate inhibitor" as used herein refers to a hydrate inhibitor stream which has not yet been subject to a substantial regeneration and/or reclamation process and which therefore comprises in addition to the hydrate inhibitor significant amounts of water, hydrocarbons, and dissolved salts in addition to dissolved heavy metal salts. The salts in addition to the heavy metal salts include monovalent and divalent cations, such as cations of alkali metals and alkali earth metals, Fe-ions etc. and anions such as halogen (Cl, Br, F, I), carbonate, hydroxide, etc. After a regeneration and/or reclamation process the hydrate inhibitor is referred to as lean hydrate inhibitor or alternatively as partly lean hydrate inhibitor if further regeneration steps are envisaged or the system does not require that substantially all salts are removed prior to reuse.

The present invention provides not only a method and system for removal of heavy metals from a hydrate inhibitor stream but more specifically a system for removal of heavy metals from a rich hydrate inhibitor stream, and providing a substantially heavy metal free rich hydrate inhibitor stream that can be regenerated into a lean hydrate inhibitor stream by conventional methods. The heavy metal salts are obtained as separate fraction whereas all other salts can be separated via conventionally systems thereby obtaining a heavy metal free salt waste stream. Accordingly the present invention provides a selective heavy metal ion removal method and system.

According to the present invention the heavy metals are separated in an upstream system providing the benefit of keeping the traditional pretreatment system, regeneration and reclamation system heavy metal free. The heavy metals are separated in a small fraction significantly smaller than the salt fractions obtained from pre-treatment and reclamation system.

The present invention introduces a three phase disc stack centrifuge separator, where hydrocarbon separation significantly increases the efficiency of the downstream processes, including pre-treatment, regeneration and reclamation. This will especially improve the performance of the gravity separator and centrifuges employed for separating divalent cation salts during pretreatment. Hydrocarbon content in the produced water is also reduced considerably, increasing the quality of the water to be disposed or further used in the process. This also minimises the complexity of the possible produced water treatment facility.

In an aspect of the present invention the three phase disc stack centrifuge can be operated at optimal flow rates, according to the following equations:
v=flow rate (m³/h)
$g_f$=the gravitational force of the centrifuge
r=ratio $$r = g_f/v \text{ and } N_1 < r < N_2$$

Where $N_1$=50 and $N_2$=350

In one aspect of the present invention the reactant is a sulphide source such as $Na_2S$. Generally it has never been considered to add sulphides to a MEG regeneration and reclamation system due to the risk of formation of toxic $H_2S$. The present inventors have however discovered that in this process, adding a sulphide may provide a selective reaction of heavy metal to precipitate as sulphide, which can be applied to solve the goals of the present invention.

BRIEF DESCRIPTION OF THE DRAWINGS

The present invention will be described in further detail with reference to the enclosed figures with examples of possible embodiments of the invention. Here.

PRINCIPAL DESCRIPTION OF THE INVENTION

Figure 1:
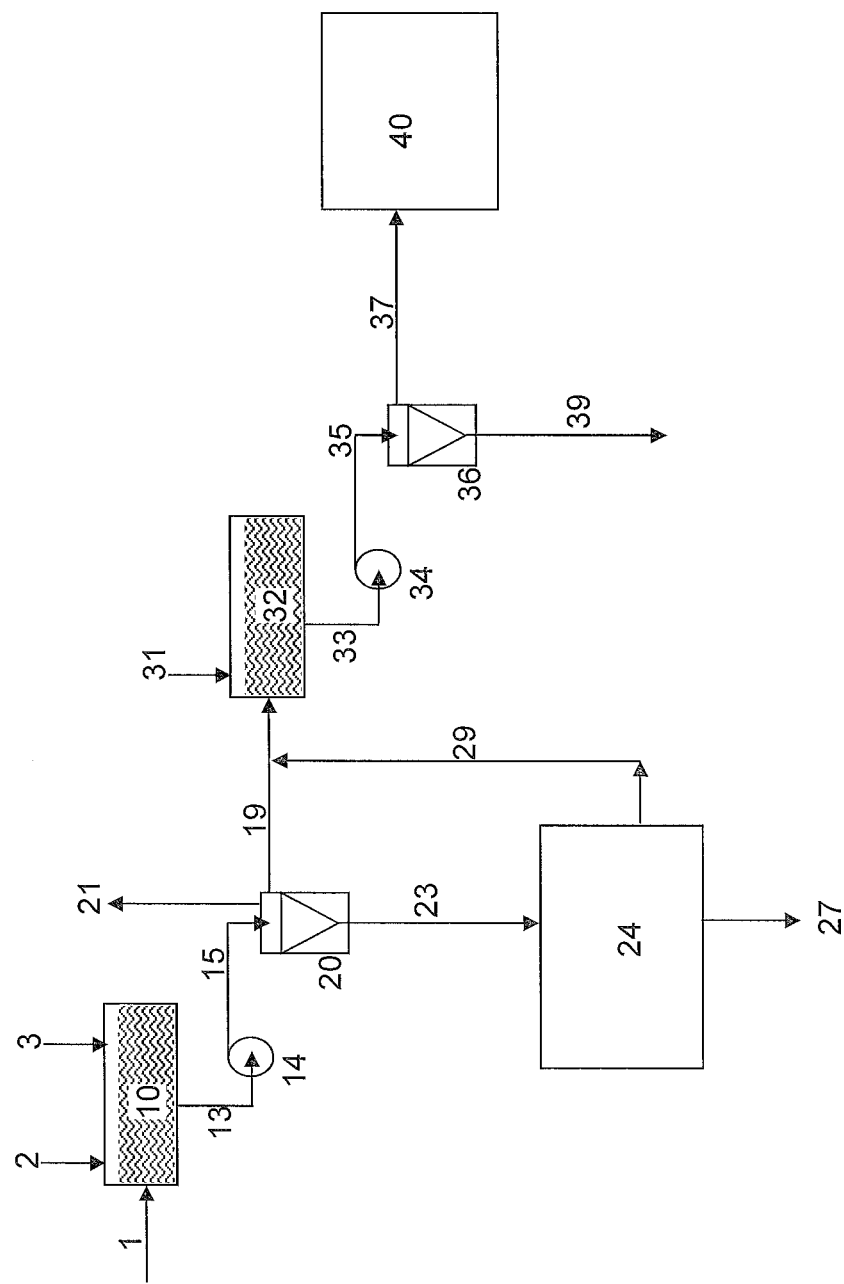
FIG. 1 illustrates schematically a first embodiment of the present invention.

The present invention will now be discussed in further detail with reference to the enclosed figures. The figures are schematic illustrations of embodiments of systems and methods according to the present invention. A person skilled in the art will understand that details such as valves, supply of heating and cooling media etc. may have been omitted to better illustrate the main principles of the present invention. In the figures equal reference signs are used to refer to equal elements. FIG. 1 shows a first embodiment of the present invention. A rich hydrate inhibitor stream 1 comprising hydrate inhibitor, water and a range of dissolved salts enters a tank 10 where the rich hydrate inhibitor is brought in contact with a stream 2 comprising a selective heavy metal reactant, in a preferred embodiment the reactant is a sulphide source such as $Na_2S$ or other sulphide salts and an optional stream 3 comprising a flocculent. The flocculent is introduced to increase particle size of the precipitate and thereby improving the particle separation. The selectivity of the reactant towards the heavy metal may be influenced by the temperature and the pH of the mixture and optionally coolers or heaters may be installed upstream the on conduit 1.

Optionally the tank 10 may be equipped with a pH control system with a possibility to regulate the pH close to neutral, pH 5-9, preferably pH=6-8, more preferably pH=6.5-7.5, which gives favourable condition for heavy metal precipitation at the same time avoid precipitation of other divalent cations such as Fe, Ca, Ba, Sr, Mg by having low temperature, below 80° C., preferably below 50° C., more preferably below 30° C. The residence time in the tank 10 is adapted to secure precipitation of the heavy metal. The reacted rich hydrate inhibitor leaves the tank via line 13 and pump 14, the rich hydrate inhibitor is fed to a three-phase disk stack centrifuge 20 through line 15. This three phase separator provides not only separation of the precipitated heavy metal salts from the hydrate inhibitor but also separation of remaining hydrocarbons. The hydrocarbons are removed through line 21, the heavy metal free rich hydrate inhibitor through line 19 and the slurry containing the heavy metal particles through line 23 which feds the slurry to a second separation system 24 providing solid liquid separation. The liquid phase comprising particle free rich hydrate inhibitor is via line 29 combined with the main rich hydrate inhibitor stream 19. The obtained concentrated heavy metal salt particles 27 will be handled further as hazardous waste.

The combined rich hydrate inhibitor streams now enter what can be considered a traditional pretreatment system consisting of an initial tank 32 for precipitation of salts of divalent cations. The alkalinity in the tank 32 is controlled by addition of base through line 31. Examples of applicable bases include: $Na_2CO_3$, $K_2CO_3$, KOH, NaOH. An appropriate resident time to secure precipitation of the divalent cation salts is obtained through the tank 32. From here the rich hydrate inhibitor is transferred via line 33, pump 34 and line 35 to a second centrifuge 36, preferably a disk stack centrifuge. Due to the earlier removal of remaining hydrocarbons the centrifuge 36 or gravity separator (not shown) will show improved performance. Stream 39 contains the separated divalent cation salts, whereas stream 37 contains partly rich hydrate inhibitor which is being fed to a traditional regeneration and reclamation system 40 providing conventional full stream or slipstream reclamation. The particles in stream 39 are non hazardous and neither are the monovalent cation salts that are removed from the hydrate inhibitor during reclamation.

Figure 2:
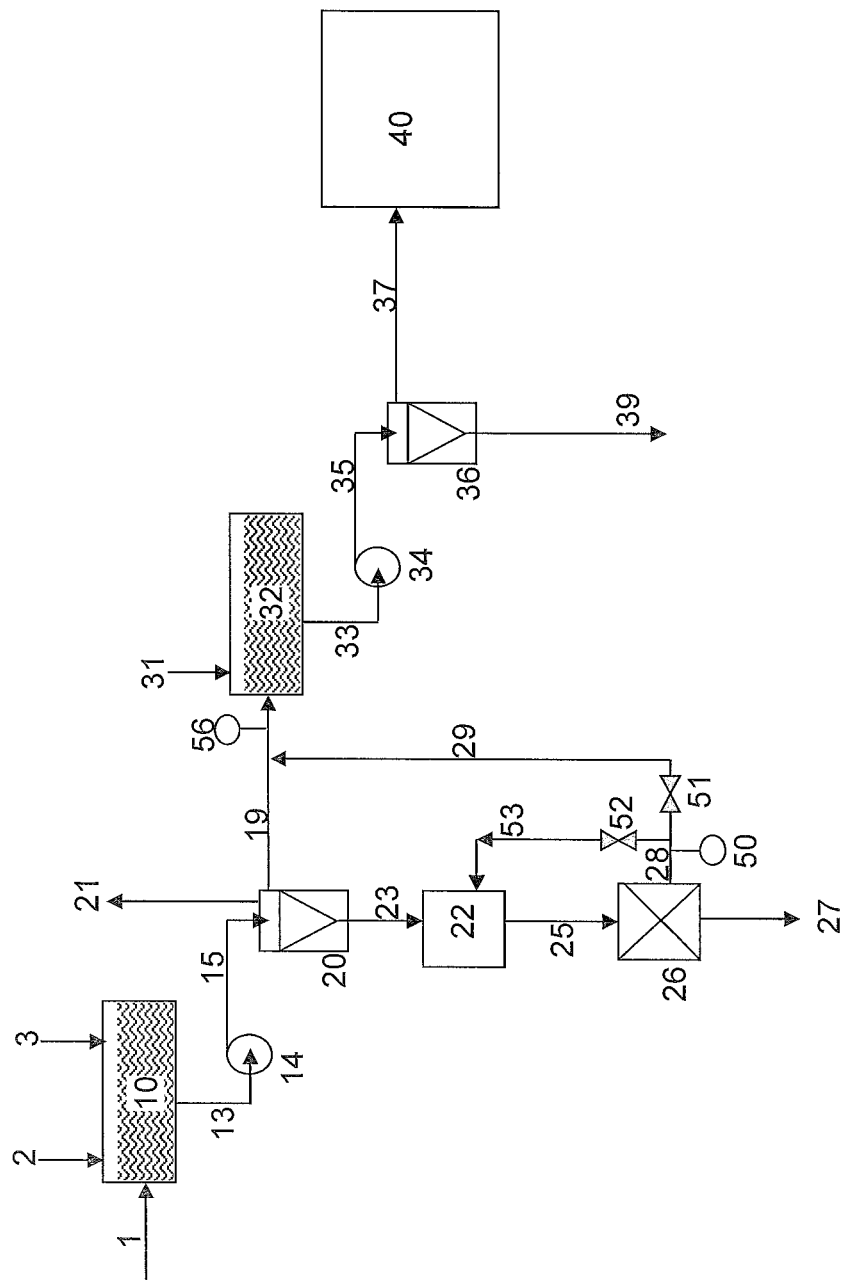
FIG. 2 illustrates schematically a second embodiment of the present invention.

FIG. 2 illustrates another embodiment of the present invention wherein an embodiment of the particle separation system is described in further detail. Here the slurry stream 23 enters a buffer tank 22 from where it is being fed to a solid-liquid separation unit 26. Solid-liquid separation unit 26 can be but is not limited to filter, basket centrifuge etc. In a start-up situation the unit 26 may not provide acceptable separation and the liquid phase 28 is then return via valve 52 and line 53 to the buffer tank 22. The quality of the separation is monitored by a sensor 50. When the stream quality is increased and the valve 51 can be opened and the valve 52 closed. Stream 27 will be nearly dry cake of precipitated heavy metal, which can be disposed off safely.

Also illustrated on FIG. 2 is the optional installation of a second sensor or sampling unit 56 for measuring the efficiency of the heavy metal removal to avoid heavy metals from entering the pretreatment system.

Figure 3:
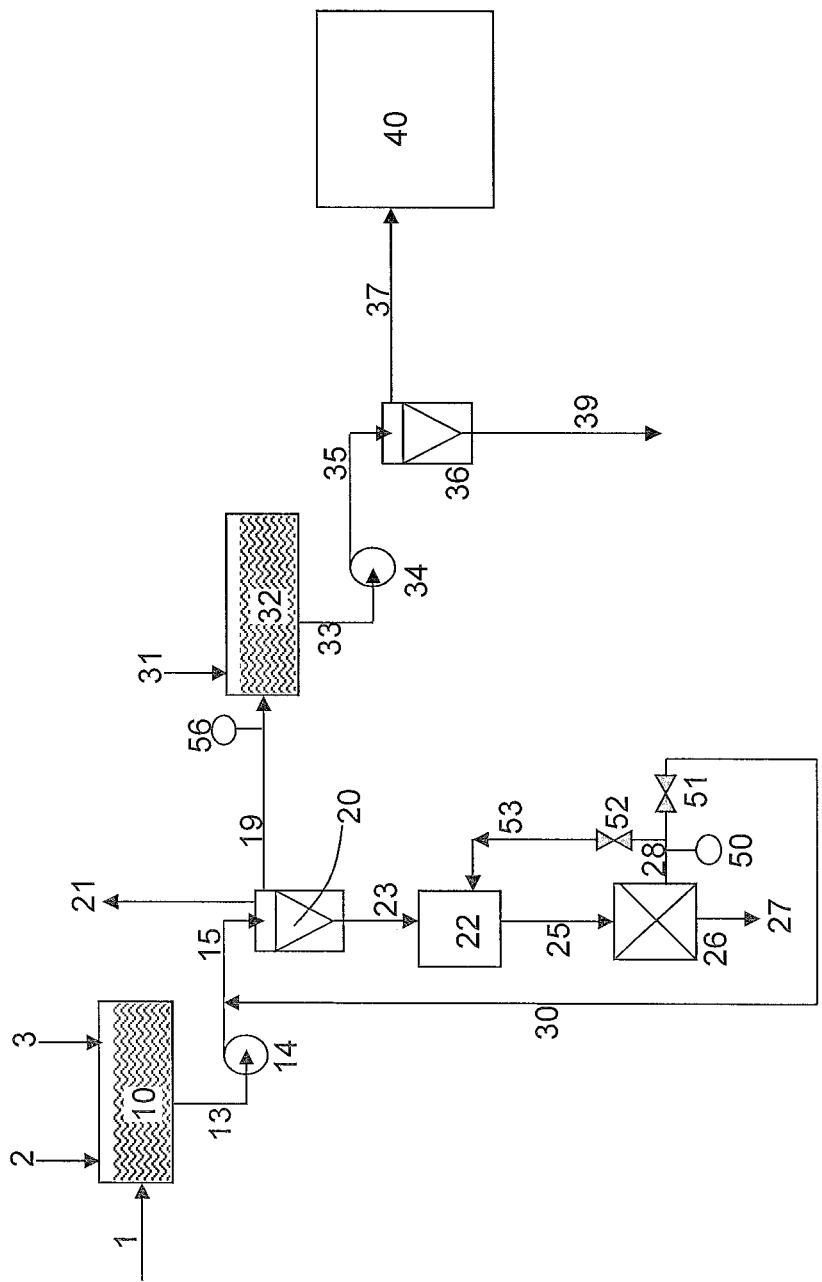
FIG. 3 illustrates schematically a third embodiment of the present invention.

FIG. 3 illustrates an alternative embodiment of the present invention. Equal units are given equal reference signs. The difference compared to FIGS. 1 and 2 is that the liquid stream from the separation system leaving through valve 51 is passed as stream 30 back into the line 15. This system provides the further advantage that in case that heavy metal particles are allowed to pass the filter they will be passed back to the three phase separator 20 and be separated of again. In this embodiment the valve 52 and the line 53 may be obsolete.

Figure 4:
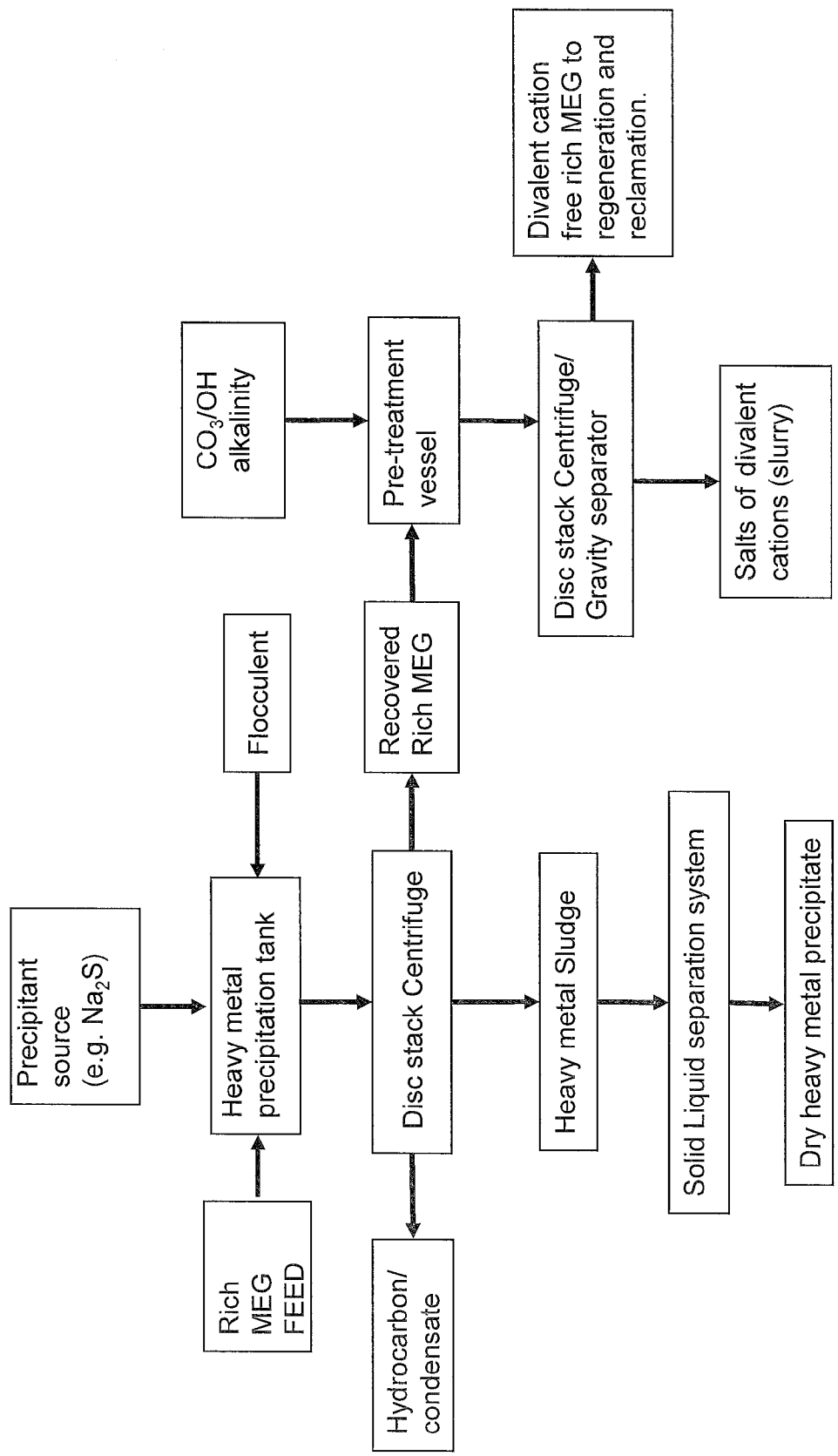
FIG. 4 shows a block diagram of an embodiment of the present invention.

FIG. 4 illustrates an embodiment of the present invention as a block diagram. In this embodiment the hydrate inhibitor is mono ethylene glycol (MEG). A rich MEG feed is fed to a heavy metal precipitation tank to which a precipitant source/reactant e.g. $Na_2S$ and flocculent to increase the size and separation of the particles is also fed. The reacted mixture is passed on to a disc stack centrifuge providing separation into three streams, a hydrocarbon/condensate stream, a recovered rich MEG stream and a Heavy metal sludge stream. The heavy metal sludge stream is separated in a solid-liquid separation system providing nearly dry heavy metal precipitate. The solid-liquid separation reduces the rest stream comprising the hazardous mercury to a minimum. The recovered rich MEG enters the pretreatment vessel wherein the alkalinity is controlled to provide for precipitation of salts of divalent cations. The salts are removed in a disk stack centrifuge or a gravity separator providing a divalent cation free rich MEG to regeneration and reclamation and a slurry comprising salts of divalent cations. This slurry will not contain hazardous mercury and therefore need not be treated accordingly.

The invention claimed is:

1. A method for removal of heavy metal ions from a rich hydrate inhibitor stream, wherein the method comprises:
   a) adding a selective heavy metal reactant to the rich hydrate inhibitor stream, forming a fluid stream comprising heavy metal salt particles,
   wherein the selective heavy metal reactant is a sulphide;
   b) separating the obtained fluid stream into three streams: a hydrocarbon stream, a recovered rich hydrate inhibitor stream, and a slurry comprising the heavy metal salt particles; and
   c) separating remaining hydrate inhibitor from the slurry thereby obtaining a concentrated rest comprising the heavy metal salt particles.

2. The method according to claim 1, wherein the separation in step b) is performed in a disc stack centrifuge.

3. The method according to claim 1, wherein the method comprises regulating the pH of the rich hydrate inhibitor stream to between 6 and 8.

4. The method according to claim 1, wherein the method comprises regulating the temperature of the rich hydrate inhibitor stream to below 50° C.

5. The method according to claim 1, wherein the heavy metal is selected from the group consisting of mercury, cadmium, lead, chromium, cobalt, arsenic, nickel, manganese, and copper.

6. The method according to claim 1, wherein the method comprises combining the remaining hydrate inhibitor with the recovered rich hydrate inhibitor stream.

7. The method according to claim 1, wherein the method further comprises downstream precipitation and removal of divalent cation salts from the recovered rich hydrate inhibitor stream.

8. The method according to claim 1, wherein the sulphide is $Na_2S$.

9. The method according to claim 1, wherein the method further comprises adding a flocculent to the rich hydrate inhibitor stream.

10. The method according to claim 1, wherein the hydrate inhibitor is mono-ethylene glycol (MEG).

* * * * *